United States Patent
Muse, Jr. et al.

(10) Patent No.: US 8,048,919 B2
(45) Date of Patent: Nov. 1, 2011

(54) USE OF ETHYL LACTATE AS AN EXCIPIENT FOR PHARMACEUTICAL COMPOSITIONS

(75) Inventors: Joel Muse, Jr., Annapolis, MD (US); Howard A. Colvin, Decatur, IL (US)

(73) Assignee: Archer Daniels Midland Company, Decatur, IL (US)

( * ) Notice: Subject to any disclaimer, the term of this patent is extended or adjusted under 35 U.S.C. 154(b) by 1867 days.

(21) Appl. No.: 11/131,278

(22) Filed: May 17, 2005

(65) Prior Publication Data

US 2005/0287179 A1 Dec. 29, 2005

Related U.S. Application Data

(60) Provisional application No. 60/583,439, filed on Jun. 28, 2004.

(51) Int. Cl.
*C07C 69/66* (2006.01)
*A61K 31/22* (2006.01)

(52) U.S. Cl. ......................................... 514/546; 560/179
(58) Field of Classification Search .................. 560/179; 514/546

See application file for complete search history.

(56) References Cited

U.S. PATENT DOCUMENTS

| 4,243,831 | A | | 1/1981 | Malley et al. | |
|---|---|---|---|---|---|
| 4,857,525 | A | * | 8/1989 | Philippe et al. | 514/227.5 |
| 5,389,681 | A | | 2/1995 | Galli | |
| 5,439,923 | A | * | 8/1995 | Cullinan | 514/324 |
| 6,534,549 | B1 | | 3/2003 | Newton et al. | |
| 7,329,354 | B2 | * | 2/2008 | Mullee | 210/660 |
| 2005/0175644 | A1 | | 8/2005 | Vachy | |

FOREIGN PATENT DOCUMENTS

| JP | 1996-12621 A | 1/1996 |
|---|---|---|
| WO | 03106599 A1 | 12/2003 |

OTHER PUBLICATIONS

Gessner G. Hawley, the Condensed Chemical Dictionary, 8th ed.,1971, p. 522, 3 pages.*

* cited by examiner

*Primary Examiner* — Taylor Victor Oh
(74) *Attorney, Agent, or Firm* — Andrew F. Nilles

(57) ABSTRACT

This invention is based upon the unexpected discovery that ethyl lactate can be used as an emulsifying/dispersing excipient for numerous biologically active compounds without destroying the pharmacological activity of the active ingredient. Ethyl lactate proves to be an extremely effective agent for solubilizing biologically active compounds that are difficult to solubilize in conventional excipients. The operability of this invention is predicated on the necessity for the ethyl lactate to be essentially free of peroxide compounds. Such pharmaceutical grade ethyl lactate can be made by reducing the level of peroxide compounds in high purity ethyl lactate by hydrogenation, reduction with a non-catalytic chemical reducing agent, absorption into activated carbon or alumina, or distillation. In any case, it has been determined to be critical for the level of peroxide compounds to be reduced to less than 10 ppm for the pharmaceutical grade ethyl lactate to be viable as an excipient for many biologically active ingredients. The present invention more specifically discloses a pharmaceutical composition which is comprised of a biologically active ingredient wherein said biologically active ingredient is dispersed in ethyl lactate and wherein said ethyl lactate contains no more than 10 ppm of peroxidic materials and maintains a Gardner 1 color rating throughout its shelf-life period.

15 Claims, No Drawings

US 8,048,919 B2

USE OF ETHYL LACTATE AS AN EXCIPIENT FOR PHARMACEUTICAL COMPOSITIONS

This application claims the benefit of U.S. Provisional Patent Application Ser. No. 60/583,439, filed on Jun. 28, 2004, and incorporates the teachings thereof herein by reference in their entirety.

BACKGROUND OF THE INVENTION

Some medicinally active pharmaceutical compositions can be administered directly to humans and animals without the need for an excipient. For instance, aspirin can be pressed into a tablet which has sufficient mechanical integrity to remain intact during packaging, shipping and storage prior to ingestion. However, most biologically active compounds require an excipient for effective administration. For instance, many biologically active compounds require a binder, disintegrant, lubricant, coating agent, emulsifying agent or filler to be commercially viable as a pharmaceutical product.

Today, some chemical compounds that offer promising results as pharmacological agents are complex structures that are difficult to solubilize by any emulsifying/dispersing agents that are acceptable for utilization as excipients. The inability to disperse such compounds in a conventional excipient can destroy the viability of the compound for utilization as a pharmaceutical product. This is, of course, because it is critical to disperse such compounds in an agent that will allow proper and effective bioavailability.

Excipients are frequently required for stabilizing blends of liquid biologically active compounds that are not mutually soluble. Excipients which are capable of suspending and/or dispersing the biologically active compound are also commonly used to improve the bioavailability of lipid soluble compounds. In many cases, excipients that are capable of solubilizing a biologically active compound can be used to improve the efficacy of the biological agent by virtue of more efficient delivery.

The dispersibility of biologically active compounds that are difficult to solubilize can often be improved by reducing the particle size of the chemical agent. The dispersibility of such agents can also sometimes be improved by utilizing an optimal emulsifying/dispersing excipient. The solubility of some biologically active agents such as celecoxib (the cyclooxygenase-2 inhibitor found in Celebrex) can also be improved by controlling the crystal structure of the active ingredient. However, in many cases, even though a stable dispersion may form, the bioavailability of the active ingredient may still be limited. For instance, an insoluble but dispersed biologically active agent might be ingested and passed completely through the gastrointestinal tract of the subject being treated without any of the active ingredient being absorbed by the subject. Accordingly, the biologically active agent would be totally ineffective even though it might be in the form of a stable liquid dispersion.

SUMMARY OF THE INVENTION

This invention is based upon the unexpected discovery that ethyl lactate can be used as a dissolving/dispersing excipient for numerous biologically active compounds without destroying, or even hindering, the pharmacological activity of the active ingredient. Ethyl lactate proves to be an extremely effective agent for solubilizing biologically active compounds that are difficult to solubilize in conventional excipients. It can accordingly be used to solubilize biologically active agents that would otherwise be difficult or impossible to effectively deliver to a subject. The operability of this invention is predicated on the necessity for the ethyl lactate to be essentially free of peroxidic compounds, such as peroxides and hydroperoxides.

Such pharmaceutical grade ethyl lactate can be made by reducing the level of peroxide compounds in high purity ethyl lactate by distillation, hydrogenation, reduction with a non-catalytic chemical reducing agent or absorption/adsorption into activated carbon or alumina. In any case, it has been determined to be critical for the level of peroxidic compounds to be reduced to less than 10 ppm for the pharmaceutical grade ethyl lactate to be viable as an excipient for many biologically active ingredients. It is preferred for the level of peroxidic compounds to be less than 2 ppm and most preferably less than 0.5 ppm.

Unfortunately, peroxides form in situ in conventional high purity ethyl lactate which may typically contain from about 100 ppm to about 200 ppm of such peroxidic materials. It has been determined that the formation of even low levels of such peroxidic materials can destroy the activity of many biologically active agents. It is accordingly critical to preclude the generation of peroxide compounds in pharmaceutical grade ethyl lactate. It has been determined that the formation of peroxide compounds can be completely or virtually eliminated by adding a small amount (0.01 weight percent to 5 weight percent) of a pharmaceutical grade antioxidant to the ethyl lactate.

The present invention more specifically discloses a pharmaceutical grade ethyl lactate composition which is comprised of ethyl lactate and from about 0.1 to about 5 weight percent of a pharmaceutical grade antioxidant wherein the composition contains no more than about 10 ppm of peroxidic materials. Butylated hydroxytoluene is a highly preferred antioxidant that can be used for this purpose and it was unexpectedly discovered that pharmaceutical grade ethyl lactate compositions that contain it maintain a Gardner 1 color rating (remain water white) throughout their shelf-life.

The subject invention also reveals a pharmaceutical composition which is comprised of a biologically active ingredient wherein said biologically active ingredient is dispersed or dissolved in ethyl lactate and wherein said ethyl lactate contains no more than 10 ppm of peroxidic materials.

The present invention further discloses a process for making a pharmaceutical grade ethyl lactate comprising (1) hydrogenating high purity ethyl lactate in the presence of hydrogen and a hydrogenation catalyst to produce a peroxide-free ethyl lactate and (2) adding 0.01 to about 5 weight percent of a pharmaceutical grade antioxidant to the essentially peroxide-free ethyl lactate to produce the pharmaceutical grade ethyl lactate.

The present invention further reveals a process for making a pharmaceutical grade ethyl lactate comprising (1) treating high purity ethyl lactate with activated carbon to produce a peroxide-free ethyl lactate and (2) adding 0.01 to about 5 weight percent of a pharmaceutical grade antioxidant to the essentially peroxide-free ethyl lactate to produce the pharmaceutical grade ethyl lactate.

The subject invention further reveals a process for making a pharmaceutical grade ethyl lactate comprising (1) treating high purity ethyl lactate with alumina to produce a peroxide-free ethyl lactate and (2) adding 0.01 to about 5 weight percent of a pharmaceutical grade antioxidant to the essentially peroxide-free ethyl lactate to produce the pharmaceutical grade ethyl lactate.

The subject invention also discloses a process for making a pharmaceutical grade ethyl lactate comprising (1) producing an essentially peroxide-free ethyl lactate which contains no more than 10 ppm of peroxidic material by treating high purity ethyl lactate with at least one peroxide reduction technique selected from the group consisting of distillation, hydrogenation, absorption/adsorption, and chemical treatment, and (2) adding 0.01 to about 5 weight percent of a pharmaceutical grade antioxidant to the essentially peroxide-free ethyl lactate to produce the pharmaceutical grade ethyl lactate.

The present invention further reveals a process for making a pharmaceutical grade ethyl lactate comprising (1) distilling food grade ethyl lactate to produce an essentially peroxide-free ethyl lactate and (2) adding 0.01 to about 5 weight percent of a pharmaceutical grade antioxidant to the essentially peroxide-free ethyl lactate to produce the pharmaceutical grade ethyl lactate. Such pharmaceutical grade ethyl lactate will additionally contain less than 100 ppb of total metals, and less than 50 parts per billion of aluminum, less than 50 parts per billion of chromium, less than 50 parts per billion of magnesium, less than 50 parts per billion of manganese, less than 50 parts per billion of copper, less than 50 parts per billion of zinc, less than 50 parts per billion of iron, less than 50 parts per billion of lead, less than 50 parts per billion of cobalt, less than 50 parts per billion of nickel, and less than 50 parts per billion of calcium.

The subject invention also discloses a pharmaceutical grade ethyl lactate composition which is comprised of ethyl lactate and from about 0.01 to about 5 weight percent of a pharmaceutical grade antioxidant wherein the composition contains no more than about 10 ppm of peroxidic materials. Typically, such pharmaceutical grade ethyl lactate compositions are essentially void of ethyl pyruvate.

DETAILED DESCRIPTION OF THE INVENTION

Conventional high purity ethyl lactate is normally utilized as the starting material for production of pharmaceutical grade ethyl lactate in accordance with the process of this invention. Such high purity ethyl lactate is at least 99% pure and contains less than 100 ppb of total metals. High purity ethyl lactate also contains less than 50 parts per billion of aluminum, less than 50 parts per billion of chromium, less than 50 parts per billion of magnesium, less than 50 parts per billion of manganese, less than 50 parts per billion of copper, less than 50 parts per billion of zinc, less than 50 parts per billion of iron, less than 50 parts per billion of lead, less than 50 parts per billion of cobalt, less than 50 parts per billion of nickel, and less than 50 parts per billion of calcium.

The high purity ethyl lactate that can be utilized as a starting material is generally made by purification of food grade ethyl lactate by fractional distillation. Food grade ethyl lactate is at least 98% pure, has a maximum acid value of 1.0, a refractive index of 1.410-1.420, and a specific gravity of 1.029-1.032. The fractional distillation removes impurities including organic contaminates and metals. Such high purity ethyl lactate is available from commercial sources including Riba Fairfield, Inc., in Decatur, Ill. However, high purity ethyl lactate can contain quantities of peroxidic compounds in excess of 10 ppm (parts per million) and typically contains from about 100 ppm to about 200 ppm of peroxidic compounds after storage. Low purity ethyl lactate can also be used as a starting material. However, the use of low purity ethyl lactate normally requires additional purification steps, such as additional distillation, to attain the level of purity required. For instance, low purity ethyl lactate can be distilled to attain food grade ethyl lactate which in turn can be further distilled in one or more steps to attain high purity ethyl lactate.

It has been determined that peroxide compounds can destroy the effectiveness of pharmacologically active chemical compounds. Accordingly, it has been determined that peroxidic compounds at levels of greater than 10 ppm cannot be tolerated in ethyl lactate that is utilized as an excipient for pharmaceutical compositions. As a consequence of this finding, in the practice of this invention the level of peroxidic material is reduced to less than 10 ppm in ethyl lactate compositions that will be utilized as excipients for pharmaceutical compositions. It is preferred for the level of peroxidic compounds to be less than 2 ppm and more preferably less than 0.5 ppm.

In practicing this invention, a number of techniques can be employed for reducing the level of peroxidic materials in ethyl lactate compositions. This can be accomplished by fractional distillation, absorption/adsorption, chemical treatment, hydrogenation, or a combination of two or more of these techniques. For instance, high purity ethyl lactate can be treated with an absorbent, such as activated carbon or alumina, to reduce the level of peroxidic materials to below 0.5 ppm. In an alternative embodiment of this invention, the high purity ethyl lactate can be treated with a non-catalytic chemical reducing agent to produce essentially peroxide-free ethyl lactate. For purposes of this invention, ethyl lactate is deemed to be essentially peroxide-free if it contains levels of peroxidic materials below detectable limits (less than about 0.5 ppm). In another embodiment of this invention, hydrogenation is utilized to prepare essentially peroxide-free ethyl lactate from conventional high purity ethyl lactate.

Peroxide materials can be removed from high purity ethyl lactate by simply treating the high purity ethyl lactate with activated carbon and/or alumina. This can be accomplished by mixing the activated carbon or alumina throughout the ethyl lactate, such as by mixing or some alternative means for providing agitation, and subsequently removing the absorbent material from the ethyl lactate. For instance, the activated carbon or alumina could be removed from the ethyl lactate by filtration. The temperature at which such absorption techniques are conducted for removal of peroxide materials is not particularly critical. Accordingly, the ethyl lactate will normally be treated with the absorbent at or near ambient temperature. In most cases, the treatment with absorbent material will be carried out at a temperature within the range of about 10° C. to about 35° C.

Non-catalytic chemical reducing agents can also be utilized to reduce the level of peroxides in the ethyl lactate. For instance, inorganic reducing agents can be used in such a capacity. Some representative examples of inorganic reducing agents that can be used include sodium bisulfite, sodium metabisulfite, triphenyl phosphine, triethyl phosphite, lithium aluminum hydride, and sodium borohydride. Triphenyl phosphine and triethyl phosphate are examples of organic reducing agents that can be used. One method that uses non-catalytic chemical reducing agents to reduce the level of peroxides in ethyl lactate involves passing the ethyl lactate through a column that contains the chemical reducing agent. Another technique that can be used involves simply dispersing the chemical reducing agent throughout the ethyl lactate and subsequently filtering the ethyl lactate to remove residual chemical reducing agent. In cases where triphenyl phosphine or triethyl phosphate is used as the reducing agent it can simply be dissolved in the ethyl lactate being treated.

Hydrogenation of the high purity ethyl lactate is one commercially viable technique for producing pharmaceutical grade ethyl lactate that is totally peroxide-free. Such hydrogenation procedures are conducted in the presence of hydrogen and a hydrogenation catalyst, such as platinum and palladium. High pressure hydrogenation can be utilized. However, hydrogenation of the high purity ethyl lactate will typically be done under low to moderate pressure.

Precautions must be taken to prevent peroxides from forming in situ within the pharmaceutical grade ethyl lactate. It has been found that pharmaceutical grade antioxidants can be employed to accomplish this objective. It is believed that the addition of pharmaceutical grade antioxidants to ethyl lactate that contains peroxidic materials can even reduce the level of such peroxidic materials that are already present. Some representative examples of pharmaceutical grade antioxidants that can be used for this purpose include ascorbic acid, ascorbic palmitate, Vitamin E, butylated hydroxyanisole, butylated hydroxytoluene, monothioglycerol, propyl gallate, sodium ascorbate, t-butyl hydroquinone, α-lipoic acid, β-tocopherol, γ-tocopherol, δ-tocopherol, ε-tocopherol, and carnosic acid. The pharmaceutical grade antioxidant will typically be employed at a level which is within the range of about 0.01 to about 5 weight percent. The pharmaceutical grade antioxidant will more typically be employed at a level which is within the range of 0.1 to about 4 weight percent and will preferably be employed at a level which is within the range of 0.1 to 3 weight percent. It is important for the pharmaceutical grade antioxidant to be added to the ethyl lactate before it is exposed to significant amounts of air or other oxygen sources. In any case, the antioxidant will be added prior to the formation of peroxides which elevate the total level of peroxidic materials to a concentration of 10 ppm (or higher).

The pharmaceutical grade ethyl lactate which is essentially peroxide-free should be protected from peroxide formation by storing and shipping the ethyl lactate in a container that is impermeable to oxygen. It is important for the container to minimize the exposure of the pharmaceutical grade ethyl lactate to oxygen throughout the period from the time of its manufacture until utilized as an excipient in manufacturing a pharmaceutical composition. For instance, the pharmaceutical grade ethyl lactate can be stored and transported in oxygen impermeable stainless steel tanks that have been sparged with nitrogen or a noble gas. In the alternative, air can be essentially removed from the container by application of vacuum. Air can also be removed from the container by application of vacuum, followed by repressurization with nitrogen or another inert gas.

The pharmaceutical grade ethyl lactate of this invention can be utilized as a dissolving/suspending agent for biologically active ingredients. Such biologically active ingredients will typically exhibit pharmacological activity in humans and/or animals. In any case, the pharmaceutical grade ethyl lactate has excellent characteristics as a solubilizing agent for pharmaceutical compounds. The ethyl lactate can significantly improve the bioavailability of many biologically active compounds that are difficult or impossible to solubilize in conventional liquid or gel type excipients. The use of ethyl lactate as an excipient improves the delivery of the biologically active compound to the targeted area of the body or its circulatory system and ultimately to reach the receptor. In other words, the pharmaceutical grade ethyl lactate of this invention provides a higher level of bioavailability when used in conjunction with certain biologically active ingredients than can be obtained utilizing conventional excipients that are capable of dispersing the active ingredient with or without the aid of a surface active agent.

Biologically active compounds that are water-insoluble or sparingly water soluble can frequently be dispersed (dispersed as used in this context includes dissolved) in the pharmaceutical grade ethyl lactate of this invention. Some examples of water-insoluble or sparingly water soluble drug products include: carbamazepine, griseofulvin, flucytosine, benorilate, sulfamethoxazole, prednisolone, danazol, megestrol acetate, prazosin HCl, quinesterol, and certain oral contraceptives. In any case, the pharmaceutical grade ethyl lactate of this invention can be used as an excipient for many classes of biologically active compounds, including antihistamines, anti-inflammatory drugs, antibiotics, contraceptives, pain-killers, anti-viral drugs, anti-fungal drugs, and the like.

This invention is illustrated by the following examples that are merely for the purpose of illustration and are not to be regarded as limiting the scope of the invention or the manner in which it can be practiced. Unless specifically indicated otherwise, parts and percentages are given by weight.

Example 1

Into a 500 ml Autoclave Engineers Zipperclave was placed 250 ml of ethyl lactate containing 100 ppm of peroxide as measured by Quantofix™ test paper. Then, 2.5 g of 5% palladium-on-carbon (54.7% water) was added. The autoclave was sealed and pressured to 100 psig of hydrogen and agitated at 650 rpm and heated to approximately 50° C. for 3½ hours. The resulting product was drained from the autoclave and filtered to remove the catalyst. The peroxide value of the resulting ethyl lactate was 0.0 as measured by the Quantofix™ test paper.

Example 2

In a 250 ml Erlenmeyer flask equipped with a magnetic stir bar was added 100 g of ethyl lactate containing 10 ppm peroxide as measured by Quantofix™ test paper (Aldrich Chemical). The 2 g of the absorbing agent identified in Table 1 was added and the contents were stirred. Peroxide values and given treatment times are also shown in Table 1.

TABLE 1

| Absorbant | Treatment Time (minutes) | Peroxide level (ppm) |
| --- | --- | --- |
| Silica gel | 0 | 10 |
|  | 30 | 10 |
| Carbon Black* | 0 | 10 |
|  | 30 | 2-3 |
|  | 60 | 0.5 max |
| Carbon Black** | 0 | 10 |
|  | 20 | 10 |
|  | 1440 | 0 |
| Diatomaceous earth | 0 | 10 |
|  | 30 | 10 |
| Alumina | 0 | 10 |
|  | 30 | 2-5 |
|  | 60 | 2 |

*CR1240A
**CB1240B-AW

It is apparent from Table 1 that the specific absorbents tested have different levels of ability to remove peroxides from ethyl lactate. Table 1 shows that carbon black was the most effective followed by alumina.

Example 3

In a 250 ml three-neck flask was placed 100 ml of ethyl lactate containing 10 ppm of peroxide as measured by the Quantofix™ test paper. Then, the ethyl lactate was batch distilled at atmospheric pressure with a nitrogen sweep. The forerun of the distillation was 25 ml and contained 10 ppm peroxide. The middlecut of the distillation was found to contain 0.5 ppm of the peroxide.

Example 4

In this experiment, high purity ethyl lactate was treated with either butylated hydroxyl toluene (BHT), cysteine, or methionine and subsequently, exposed to an air environment to determine resistance to peroxide formation. In the procedure used, 250 ml of high purity ethyl lactate containing 0.0 ppm of peroxide as measured with Quantofix™ test paper was added to each of four beakers. The first beaker served as a control and was not treated with any chemical agent. The second beaker was treated with 0.3 g of BHT. The third beaker was treated with 0.3 g of cysteine and the fourth beaker was treated with 0.3 g of methionine. The beakers were rapidly stirred in an air atmosphere such that a large vortex resulted in each of the beakers. The level of peroxide in each of the ethyl lactate samples was monitored and is reported as a function of time in Table 2.

TABLE 2

| Time (minutes) | Control | BHT | Cysteine* | Methionine* |
|---|---|---|---|---|
| 0 | 0.0 | 0.0 | 0.0 | 0.0 |
| 15 | 0.0 | 0.0 | 0.0 | 0.0 |
| 30 | 0.0 | 0.0 | 0.0 | 0.0 |
| 60 | 0.5 | 0.0 | 0.0 | 0.5 |
| 75 | 0.5 | 0.0 | 0.0 | 0.5-2.0 |
| 90 | 0.5 | 0.0 | 0.0 | 0.5-2.0 |
| 105 | 0.5-2.0 | 0.0 | 0.0 | 2.0 |
| 120 | 0.5 | 0.0 | 0.0 | 2.0 |
| 150 | 0.5 | 0.0 | 0.0 | 2.0 |
| 180 | 0.5-2.0 | 0.0 | 0.0 | 5.0 |
| 240 | 2.0 | 0.0 | 0.0 | 2.0-5.0 |
| 300 | 0.5 | 0.0 | 0.0 | 5.0 |
| 360 | 2.0 | 0.0 | 0.0 | 5.0 |
| 1440 | 5.0 | 0.0 | 0.0-0.5 | 5.0 |

*It should be noted that some of the cysteine and methionine did not completely dissolve into the ethyl lactate.

The ethyl lactate that was stabilized with BHT proved to have good color stability and remained water white throughout the trial period. In other words, the ethyl lactate maintained a Gardner 1 color rating throughout the trial period. This was unexpected since the utilization of BHT normally results in a yellow discoloration of the material being stabilized. The BHT also proved to be the most effective of the compounds evaluated as stabilizers for pharmaceutical grade ethyl lactate against peroxide generation.

Example 5

High purity ethyl lactate is prepared by continuous distillation of food grade ethyl lactate through a column packed with structured packing under a vacuum of 28 inches of mercury over a boiling range of 84-85° C. The ethyl lactate vapors were condensed, passed through a 10 micron cartridge filter and transferred to a 55 gal polyethylene drum. BHT was added at a level of 0.25% to produce the pharmaceutical grade ethyl lactate. The drum was flushed with nitrogen and capped. The ethyl lactate had a Gardner 1 color number and was further analyzed with the following results: 99.9% ethyl lactate, 0.013% water, 100% enantiomeric purity, 0.0 parts per million peroxide, 0.07 Acidity (as measured by Food Chemical Codex protocol). Analysis for metals by ICP showed:

| | |
|---|---|
| Aluminum | <1.0 ppb |
| Calcium | 1.4 ppb |
| Chromium | <1.0 ppb |
| Copper | <1.0 ppb |
| Iron | 1.1 ppb |
| Lead | <1.0 ppb |
| Magnesium | <1.0 ppb |
| Manganese | <1.0 ppb |
| Nickel | <1.0 ppb |
| Zinc | <1.0 ppb |

While certain representative embodiments and details have been shown for the purpose of illustrating the subject invention, it will be apparent to those skilled in this art that various changes and modifications can be made therein without departing from the scope of the subject invention.

What is claimed is:

1. A pharmaceutical grade ethyl lactate composition consisting of:
   ethyl lactate; and
   from about 0.01 to about 5 weight percent of a pharmaceutical grade antioxidant;
   wherein the pharmaceutical grade ethyl lactate composition contains no more than about 10 ppm of peroxidic materials.

2. The pharmaceutical grade ethyl lactate composition of claim 1, wherein the ethyl lactate is essentially void of ethyl pyruvate.

3. The pharmaceutical grade ethyl lactate composition of claim 1, wherein the ethyl lactate contains less than 50 parts per billion of aluminum, less than 50 parts per billion of chromium, less than 50 parts per billion of magnesium, less than 50 parts per billion of manganese, less than 50 parts per billion of copper, less than 50 parts per billion of zinc, less than 50 parts per billion of iron, less than 50 parts per billion of lead, less than 50 parts per billion of cobalt, less than 50 parts per billion of nickel, and less than 50 parts per billion of calcium.

4. The pharmaceutical grade ethyl lactate composition of claim 3, wherein the pharmaceutical grade antioxidant is selected from the group consisting of ascorbic acid, ascorbic palmitate, Vitamin E, butylated hydroxyanisole, butylated hydroxytoluene, monothioglycerol, propyl gallate, sodium ascorbate, t-butyl hydroquinone, α-lipoic acid, β-tocopherol, γ-tocopherol, δ-tocopherol, ε-tocopherol, and carnosic acid.

5. The pharmaceutical grade ethyl lactate composition of claim 4, wherein the pharmaceutical grade antioxidant is the butylated hydroxytoluene.

6. The pharmaceutical grade ethyl lactate composition of claim 5, wherein the pharmaceutical grade ethyl lactate composition has a Gardner 1 color rating.

7. The pharmaceutical grade ethyl lactate composition of claim 5, wherein the pharmaceutical grade ethyl lactate composition contains no more than about 2 ppm of peroxidic materials.

8. The pharmaceutical grade ethyl lactate composition of claim 5, wherein the pharmaceutical grade ethyl lactate composition contains no more than 0.5 ppm of peroxidic materials.

9. The pharmaceutical grade ethyl lactate composition of claim 5, wherein the pharmaceutical grade ethyl lactate composition contains less than 100 parts per billion of total metals.

10. The pharmaceutical grade ethyl lactate composition of claim 5, wherein the pharmaceutical grade ethyl lactate composition contains no more than 0.5 ppm of peroxidic materials, and wherein the pharmaceutical grade ethyl lactate contains less than 100 parts per billion of total metals.

11. A composition consisting of:
ethyl lactate; and
an antioxidant selected from the group consisting of ascorbic acid, ascorbic palmitate, vitamin E, monothioglycerol, propyl gallate, sodium ascorbate, α-lipoic acid, carnosic acid and combinations of any thereof;
wherein the composition contains no more than 10 ppm of peroxidic materials.

12. The composition of claim 11, wherein the composition contains no more than 2 ppm of the peroxidic materials.

13. The composition of claim 11, wherein the composition contains no more than 0.5 ppm of the peroxidic materials.

14. A composition comprising:
ethyl lactate; and
means for reducing the level of peroxidic material in the ethyl lactate selected from the group consisting of alumina, sodium bisulfate, sodium metabisulfite, triphenyl phosphine, triethyl phosphate, and sodium borohydride;
wherein the ethyl lactate contains no more than about 10 ppm of peroxidic materials.

15. The composition of claim 14, wherein the means for reducing the level of peroxidic material in the ethyl lactate is the alumina.

* * * * *